US008910825B2

(12) United States Patent
Austin et al.

(10) Patent No.: US 8,910,825 B2
(45) Date of Patent: Dec. 16, 2014

(54) APPARATUS AND METHOD FOR NON-INTRAVENOUSLY ADMINISTERING A MEDICATION

(75) Inventors: Paul R. Austin, Webster, NY (US); Frank M. Goetz, Fairport, NY (US)

(73) Assignee: Xerox Corporation, Norwalk, CT (US)

( * ) Notice: Subject to any disclaimer, the term of this patent is extended or adjusted under 35 U.S.C. 154(b) by 186 days.

(21) Appl. No.: 13/352,990

(22) Filed: Jan. 18, 2012

(65) Prior Publication Data

US 2013/0184681 A1   Jul. 18, 2013

(51) Int. Cl.
G07F 11/00 (2006.01)

(52) U.S. Cl.
USPC .......................................................... 221/2

(58) Field of Classification Search
USPC ................. 604/514; 700/231–244; 221/2
See application file for complete search history.

(56) References Cited

U.S. PATENT DOCUMENTS

| 4,473,884 | A | * | 9/1984 | Behl | 700/242 |
| 4,733,971 | A | | 3/1988 | Pratt | |
| 5,805,051 | A | * | 9/1998 | Herrmann et al. | 340/309.4 |
| 6,594,549 | B2 | | 7/2003 | Siegel | |
| 7,137,528 | B1 | * | 11/2006 | Yates et al. | 221/82 |
| 7,295,890 | B2 | * | 11/2007 | Jean-Pierre | 700/244 |
| 7,689,318 | B2 | * | 3/2010 | Draper | 700/236 |
| 7,844,363 | B1 | | 11/2010 | Mehdizadeh | |
| 2004/0215369 | A1 | * | 10/2004 | Rosenblum | 700/235 |
| 2008/0300718 | A1 | * | 12/2008 | Austin et al. | 700/235 |

OTHER PUBLICATIONS

McKesson PROmanager-RX, McKesson, http://www.mckesson.com/en_us/McKesson.com/For%2BPharmacies/Inpatient/Pharmacy%2BAutomation/PROmanager-Rx.html (2012).
Canna MedBox, Prescription Vending Machines, Inc. DBA Medicine Dispensing Systems, http://www.cannamedbox.com (2012).

* cited by examiner

*Primary Examiner* — Nicholas Lucchesi
*Assistant Examiner* — Diva K Chander
(74) *Attorney, Agent, or Firm* — Simpson & Simpson, PLLC (57) ABSTRACT

A computer-based apparatus for dispensing a medication, including: at least one specially programmed computer; and a medication device. The at least one computer is arranged to automatically generate a medication regimen for a patient, the medication regimen including designation of a measure for an orally-administered or injectable medication; or automatically modify a medication regimen for a patient, by modifying a designation of a measure for an orally-administered or injectable medication. The medication device is arranged to: extract the orally-administered or injectable medication from a medication storage element; and non-intravenously dispense an amount of the orally-administered or injectable medication equal to the designated measure or the modified designated measure into a container. The at least one specially programmed computer is part of the medication device, is attached to the medication storage element, or is located remote from the medication device.

17 Claims, 2 Drawing Sheets

APPARATUS AND METHOD FOR NON-INTRAVENOUSLY ADMINISTERING A MEDICATION

TECHNICAL FIELD

The present disclosure relates to an apparatus and method for non-intravenously metering and administering a medication, in particular, dynamically calculating a regimen for the medication. The present disclosure also related to an apparatus and method for enabling communication and data exchange among parties associated with implementing the regimen.

BACKGROUND

Medication errors for orally-administered or injectable medications are a common occurrence in both in-patient and out-patient settings. As the population ages and treatment therapies become more sophisticated, medication regimens are becoming more complex and demanding. Further, it is often necessary to implement an iterative process in which dosages and dosage schedules are modified until a desired therapeutic effect is achieved. This process is hampered by the fact that most medications are only available with set dosage levels, which limits the variations possible. For example, an ideal dosage may be outside of the set dosage levels. Also, considerable waste may be entailed in the iterative process, since as dosage levels are modified, the remaining medications with previous dosage levels are no longer usable and are discarded.

Often medication is dispensed in pill form, requiring patients to count out pills and take a large number of pills at one time. If a dosage for a particular medication is changed, any remaining pills of the medication in the previous dose must typically be discarded, resulting in considerable waste and extra expense. Further, considerable destructive variance in schedule and dosage may occur in a self-administered environment. For example, the numbers of pills a patient takes and when the patient takes the pills are typically the responsibilities of the patient to understand and implement. Thus, a patient may take an incorrect dosage (too few or too may pills) or take a correct dosage at an incorrect time (to close to or too far from a previous dosage).

Prescription orally-administered medications in liquid form are not typically made available to individual patients or even to medical care facilities, such as clinics and hospitals, at least because such mediations are typically quite concentrated and the means for storing and accurately metering such medications in a patient or medical care facility are not available.

It is known to control dosages of intravenously administered medications, for example, using an infusion pump. However, the administration of orally-administered medications is generally restricted to liquid medications and pills available only in fixed dosage levels, and the administration of injectable medications is restricted to dosages available in fixed levels or to a manual process of extracting a medication, for example, using a syringe to extract a liquid medication from a bottle of the medication, and determining by eye when a desired amount of the liquid medication has been extracted. For injectable medications, measuring is typically done using a scale on the side of the syringe, with tick marks indicating 0.1 ccs or 0.1 mL, with a typical accuracy of +/−0.1 mL. Most dosages are rounded numbers, for example, 10 cc. Therefore, dose variation in routine nursing is in the 1-10% range. Medication concentrations tend to be calibrated to support 1-10 cc measurements.

SUMMARY

According to aspects illustrated herein, there is provided a computer-based apparatus for dispensing a medication, including: at least one specially programmed computer; and a medication device. The at least one computer is arranged to automatically generate a first medication regimen for a first patient, the first medication regimen including designation of a first measure for a first orally-administered or injectable medication; or automatically modify a first medication regimen for a first patient, by modifying a designation of a first measure for a first orally-administered or injectable medication. The medication device is arranged to: extract the first orally-administered or injectable medication from a medication storage element; and non-intravenously dispense a first amount of the first orally-administered or injectable medication equal to the first designated measure or the modified first designated measure into a container. The at least one specially programmed computer is part of the medication device not including the medication storage element, is attached to the medication storage element, or is located remote from the medication device.

According to aspects illustrated herein, there is provided an apparatus for storing and dispensing a medication, including: a cartridge including a cavity for storing an orally-administered or injectable medication; and a computer-based module generating and storing information regarding the orally-administered or injectable medication.

According to aspects illustrated herein, there is provided a computer-based method for dispensing a medication, including using at least one specially programmed computer to: automatically generate a first medication regimen for a first patient, the first medication regimen including designation of a first measure for a first orally-administered or injectable medication; or, automatically modify a first medication regimen for a first patient, by modifying a designation of a first measure for a first orally-administered or injectable medication; and transmit, to a medication device, instructions for: extracting the first orally-administered or injectable medication from a medication storage element; and non-intravenously dispensing a first amount of the first orally-administered or injectable medication equal to the first designated measure or the modified first designated measure into a container, wherein the at least one specially programmed computer is part of the medication device, is attached to the medication storage element, or is located remote from the medication device.

According to aspects illustrated herein, there is provided a computer-based method for dispensing a medication using at least one specially programmed computer to: determine an amount of an orally-administered or injectable medication present in a cartridge; compare the amount of the orally-administered or injectable medication present in the cartridge with a threshold amount; and when the amount of the orally-administered or injectable medication present in the cartridge is below the threshold amount, to generate a supply signal to initiate a process to supply, to the apparatus, another cartridge storing the orally-administered or injectable medication.

According to aspects illustrated herein, there is provided an apparatus for storing and dispensing a medication, including: a cartridge including a cavity for storing an orally-administered or injectable medication; and a module, including a specially-programmed computer, attached to the cartridge, and arranged to: determine an amount of the orally-administered or injectable medication present in the cartridge; and transmit a signal including the amount of the orally-administered or injectable medication present in the cartridge.

BRIEF DESCRIPTION OF THE DRAWINGS

Various embodiments are disclosed, by way of example only, with reference to the accompanying schematic drawings in which corresponding reference symbols indicate corresponding parts, in which.

DETAILED DESCRIPTION

Moreover, although any methods, devices or materials similar or equivalent to those described herein can be used in the practice or testing of these embodiments, some embodiments of methods, devices, and materials are now described.

The following non-limiting definitions are applicable to the present disclosure:

Dosage: an amount of an orally-administered or injectable medication to be dispensed.

Measure: an amount of an orally-administered or injectable medication expressed in terms of a known measurement system, for example, as described by a certain number of units from the measurement system. Any measurement system known in the art can be used.

Medication regimen: information and instructions regarding one or more orally-administered or injectable medications to be administered to a patient. The information and instructions can include amounts of the medications to be administered at any one time and times at which to administer amounts of the medication.

Non-intravenously: a process by which a medication is taken by mouth or injected. The process does not include intravenously administering a medication via an infusion pump or similar device.

Orally-administerable or injectable medication: a medication that is taken by mouth by a patient or that is injected, for example, subcutaneously or intramuscularly, into a patient. An orally-administered or injectable medication is not administered intravenously. An orally-administered medication can be in powder form or in liquid form.

Real time: of or relating to a computer or computer system that updates or uses information at substantially the same rate as the information is received.

Real time data: data which is received by a computer and acted upon by the computer at the same rate, for example, data described below is received by the computer described below and immediately used by the computer to calculate, re-calculate, or modify a medication regimen.

Time period: a specific point in time, for example, 3 PM; a time span, for example, two hours; a time span in terms of specific points in time, for example, 3 PM to 5 PM; a point in time with reference to a previous point in time or time span, for example, four hours after a previous dose of a medication; or time span with reference to a previous point in time or time span, for example, four to six hours after a previous dose of a medication.

Figure 1:
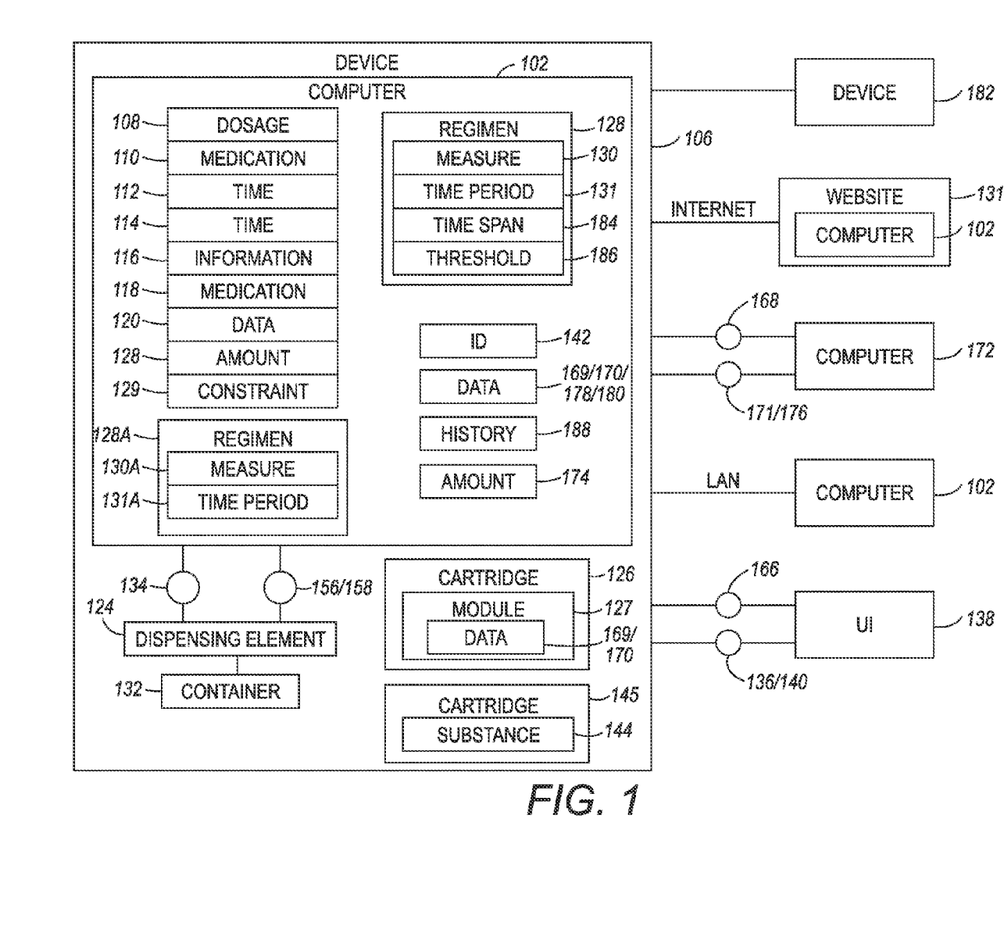
FIG. 1 is a schematic block diagram of an apparatus for non-intravenously administering a medication; and, FIG. 2 is a schematic block diagram of the dispensing element shown in FIG. 1.

FIG. 1 is a schematic block diagram of apparatus 100 for dispensing a medication. Apparatus 100 includes at least one specially programmed computer 102. Apparatus 100 also includes medication device 106. In the discussion that follows, at least one specially programmed computer 102 is interchangeable referred to as "the computer" or "computer 102." The computer is arranged to calculate, for a patient, dosage 108 for orally-administrable or injectable medication 110. In the discussion that follows, the terms "orally-administerable" and "orally-administered" are used interchangeably. In an example embodiment, the dosage is calculated by using real time data such as current point in time 112, point in time 114 at which a previous dosage of medication 110 was administered, information 116 regarding another medication 118 prescribed for the patient, or real time physiological data 120 for the patient. Medication device 106 includes dispensing element 124, arranged to extract medication 110 from medication storage element, or cartridge, 126, and non-intravenously dispense medication 110 in accordance with the dosage. In an example embodiment, cartridges 126 are insertable in and removable from device 106. Thus, after the medication in a cartridge is depleted, the cartridge can be removed and replaced with a full cartridge. In an example embodiment, a cartridge can be removed without the use of tools.

In an example embodiment, the dosage includes amount 128 of medication 110 to be dispensed, and constraint 129 regarding administration of medication 110. Constraint 129 can be any constraint known in the art, including, but not limited to: a time period in which to administer medication 110, a time of day in which to administer medication 110, considerations of food or drink previously consumed by the patient, considerations of food or drink to be consumed by the patient following administration of medication 110, or a time at which medication 118 was last taken or will next be taken.

It should be understood that computer 102 can be: on-board medication device 106 (separate from cartridge, 126); on-board cartridge 126, for example, as computer module 127; or one or more computers located at one or more locations remote from medication device 106. When computer 102 is located remote from medication device 106, the computer and medication device 106 can be electrically connected using any means known in the art, including, but not limited to, a wide area network (WAN), for example, website 131 and the Internet, a local area network (LAN), hardwire connection, or wireless connection. It should also be understood that various combinations of the functions described above and below for computer 102 can be distributed across a computer on medication device 106, module 127, or one or more computers located remote from medication device 106. In the discussion that follows, to simplify the presentation, functions and data of computer 102 are shown with computer 102 being part of medication device 106. However, it should be understood that some or all of the functions and data can be associated with module 127 or with computer 102 in one or more remote locations.

In an example embodiment, the computer is arranged to calculate or modify medication regimen 128 for the patient. In an example embodiment, the computer is arranged to calculate or modify medication regimen 128 using real time data as further described below. The regimen includes designation of measure 130 for medication 110 or designated time period 131. In an example embodiment, the dispensing element is arranged to extract medication 110 from the medication storage element and non-intravenously dispense an amount of medication 110, substantially equal to measure 130, into container 132. In an example embodiment, the dispensing element is arranged to extract medication 110 from the medication storage element and non-intravenously dispense medication 110 into container 132 during time period 131. In an example embodiment, the dispensing element is arranged to extract medication 110 from the medication storage element and non-intravenously dispense an amount of medication 110, substantially equal to measure 130, into container 132 during time period 131. In an example embodiment, container 132 is a cup or similar container for consumption of medication 110 by mouth by the patient. In an example embodiment, container 132 is for a syringe or similar device for injecting medication 110 into the patient, for example, medication 110 could be insulin for treating diabetes in the patient.

In an example embodiment, the computer is arranged to generate control signal 134 and transmit the control signal to the dispensing element. The control signal includes instructions to extract and dispense medication 110 according to regimen 128. If the computer is remotely located, the control signal can be transmitted to medication device 106 for relay to the dispensing element or can be directly transmitted to the dispensing element.

In an example embodiment, the computer receives signal 136, for example, from user interface 138. User interface 138 can include a keyboard or touch screen for accepting input to generate signal 136. Interface 138 can include an audio/visual system, including a microphone for accepting input to generate signal 136. Signal 136 includes a request to dispense medication 110. In an example embodiment, signal 136 includes identification data 140. The computer is arranged to analyze the identification data to determine if the identification data matches identity 142 for the patient subject to regimen 128. If data 140 and identity 142 match, the computer enables the dispensing of medication 110 by medication device 106.

Medication 110 can be in powdered or liquid form. In an example embodiment, depending on the composition of medication 110, either a water-based or fat-based liquid vehicle substance 144 is dispensed by dispensing element 124 to mix with medication 110 in the container. In an example embodiment, the vehicle substances are stored in one or more cartridges 145 in medication device 106. For example, an amount of medication 110 dispensed by dispensing element 124 may be so small as to make it difficult to take the medication by mouth or inject the medication. In this case substance 144 provides a desired increase in volume. Also, medication 110 may have an unpleasant flavor which would inhibit the patient from taking medication 110 by mouth, in which case substance 144 can be pleasantly flavored. Regimen 128 includes information as to whether a water-based liquid vehicle substance 144 or a fat-based liquid vehicle substance 144 is required for medication 110. The dispensing element is arranged to dispense a specified amount of the required water-based liquid vehicle substance or a fat-based liquid vehicle substance into the container.

Figure 2:
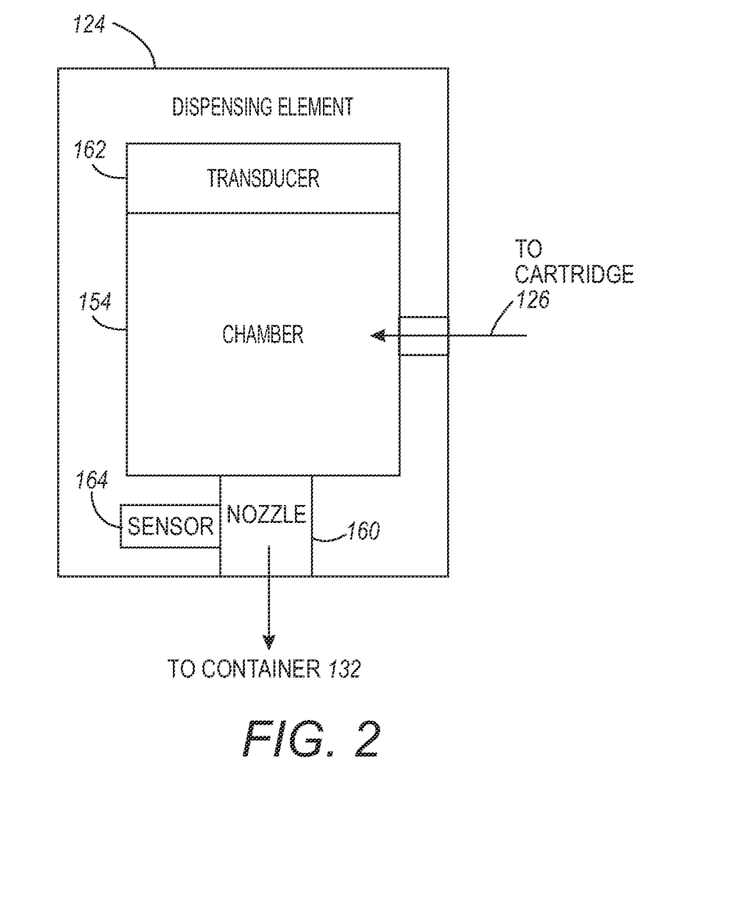

Dispensing Mechanism: FIG. 2 is a schematic block diagram of dispensing element 124 shown in FIG. 1. The following should be viewed in light of FIGS. 1 and 2. In an example embodiment, dispensing element 124 includes chamber 154 and the dispensing element is arranged to receive, at least indirectly from the computer, metering control signal 156 including instructions 158 for executing a cycle a specified number of times. The cycle includes transporting medication 110 from cartridge 126 into the chamber, and displacing a known amount of medication 110 from the chamber through a port, or nozzle, 160 to container 132. The specified number of times is such that a measure of medication 110 displaced through the nozzle is equal to amount 130. In an example embodiment, the computer is arranged to calculate the specified number of cycles. The dispensing element is arranged to transport medication 110 into the chamber using any means known in the art, including, but not limited to vacuum, gravity, or capillary action. In an example embodiment, the dispensing element includes a piezoelectric transducer 162 and the transducer is arranged to displace to expel medication 110 from the chamber, for example, in response to an applied current, at least a portion of the transducer displaces into the chamber or otherwise reduces a volume of the chamber such that medication 110 in the chamber is expelled through the nozzle.

In an example embodiment and in response to the metering control signal, the displacement element is arranged to extract medication 110 from medication cartridge 126, expel medication 110 from the chamber through the nozzle at a known flow rate, and terminate operation when the amount of medication 110 expelled through the nozzle is substantially equal to measure 130. In an example embodiment, the computer is arranged to monitor flow through the nozzle, for example via sensor 164, and determine when the amount of medication 110 expelled through the nozzle is substantially equal to measure 130. In an example embodiment, a peristaltic component is used to expel medication 110 from cartridge 126.

Patient Education and Information: Apparatus also can be used to communicate information to a patient. In an example embodiment, the user interface is arranged to communicate information 166, for example, a time at which a next dosage of medication 110 is due. In an example embodiment, the user interface is arranged to provide information 166 in response to a query. Information 166 can be any information known in the art with respect to medication 110, including, but not limited to the amount of medication 110 per dosage, the intended or therapeutic effects of medication 110, side effects of medication 110, and advisories or warning regarding taking medication 110 with other medications.

Error Prevention: In an example embodiment, the computer is arranged to identify medication 110 stored in the cartridge, determine if medication 110 stored in the cartridge is included in any medication regimen for the patient; and transmit warning signal 168 if medication 110 is not included in regimen 128 or another medication regimen for the patient. Thus, the computer provides a means for preventing administration of a medication that has not been prescribed for the patient.

In an example embodiment, module 127 provides a "handshake" to confirm that cartridge 126 is being installed in the proper device 106. For example, a remote computer 102 or computer 102 in device 106 stores data 169 such as: identification of a particular device 106; identification of a patient or patients to receive medications from the device; data regarding respective medication regimens for the patient or patients, such as medications included in the regiments; and authorizations from respective medical practitioners, prescribers, medication suppliers, and entities paying for at least a portion of the medications in the respective medication regimens. Module 127 in turn stores data 170 including at least some of data 169 or including other data to correlate with data 169. Upon installation in device 106, module 127 communicates with computer 102 and module 127 and/or computer 102 uses data 169 and 170 to confirm the identities, data, and authorizations noted above. Upon determination of confirmation, computer 102 enables metering and dispensing of the medication in the cartridge.

Inventory Control and Replenishment: In an example embodiment, the computer is arranged to identify a point in time at which the cartridge is installed in medication device 106 and compare the point in time to a time period at which it was desired or intended to install the cartridge, for example, to monitor compliance with a regimen for the patient or to monitor compliance with a schedule for provision of and payment for medication 110. The computer is arranged to transmit compliance signal 171 to computer 172 associated with an entity including, but not limited to, an insurance company, a health care provider, a health care facility, an entity supplying the medication storage element, and a health care records system, indicating whether the point in time fell within the time period. Thus, the computer provides a means for verifying whether medications are being made available in a timely fashion and also provides a means of tracking when medications are actually being made available.

In an example embodiment, computer 102 is arranged to determine an amount of medication 110 present in cartridge 126 and compare the amount to threshold amount 174. If the amount of medication 110 present in the cartridge is below amount 174, the computer generates and transmits signal 176 including data regarding medication 110 and cartridge 126. In an example embodiment, signal 176 is sent to computer 172 to initiate an automatic ordering and authorization process for providing a replacement cartridge 126, for example, computer 172 is part of an authorized order entry system. The information in signal 176 also can be used by entities associated with computer 172 to monitor the amount of medication 110 dispensed by medication device 106 and a time span within which an amount of medication 110 has been dispensed by medication device 106, for example, computer 172 is, or is part of, an electronic health record system.

Communication Nexus: In an example embodiment, the computer is the nexus for communication among the parties associated with the implementation of regimen 128. For example, apparatus 100, in particular computer 102, is the communications link among device 106 (and the patient), caregivers at the location of the patient, medical practitioners responsible for the patient, medical practitioners responsible for prescribing medication 110, a supplier of medication 110, agencies responsible for authorizing the use of medication 110 for the patient, and agencies responsible for some or all of the payment for medication 110. For example, the computer provides a means of documenting regimen 128 among the parties noted above. In an example embodiment, computer 172 is, or is part of, an electronic health record system or an authorized order entry system.

In an example embodiment, computer 102 is used in a process to coordinate prescription of, payment for, and administration of an orally-administered or injectable medication. For example, a medical practitioner enters a prescription for medication 110 into computer 102. The computer contacts a computer associated with an entity, such as an insurance company, providing some or all of the payment for medication 110, to obtain authorization from the entity. The entity transmits an authorization, as applicable, to computer 102. Based on this authorization, computer 102 proceeds with the operations described above and below.

In an example embodiment, computer 102 is used to capture, coordinate, and disseminate medical data regarding the patient. For example, computer 102 can be interfaced with one or more computers associated with one or more entities including, but not limited to, an insurance company, a health care provider, a health care facility, an entity supplying the medication storage element, and a health care records system. As regimen 128 is calculated, re-calculated, or modified, information regarding regimen 128 is transmitted to the entities noted above. Thus, the most current information regarding regimen 128 and the patient is instantly made available to a health care provider for the patient, a prescriber for the patient, a supplier of medication 110, and the entity involved in payment for medication 110 and/or medication device 106. In addition, other data can be made available to the preceding parties, for example, physiological data 178/180, and times when dosages were actually taken. In short, any information received by, generated by, or modified by computer 102 is made available to the preceding parties.

Closed Loop: In an example embodiment, the computer is arranged to receive physiological data 178 regarding the patient and calculate, using the physiological data, regimen 128. That is, the computer calculates the medication regimen based on feedback, in particular, data 178, regarding an actual condition of the patient. In an example embodiment, data 178 is used in real time by the computer to calculate regimen 128. Thus, the calculation of regimen 128 is based on current conditions as of the intended time for dispensing of medication 110.

In an example embodiment, the computer is arranged to access initial medication regimen 128A for medication 110 and the patient including initial designated unit of measure 130A or initial designated time period 131A. In an example embodiment, regimen 128A has been calculated by the computer and stored in the computer. Regimen 128A is in effect as of the receipt of data 178 by the computer and data 178 may be impacted by the previous dosage of medication 110 in accordance with regimen 128A. For example, an amount of medication 110 equal to measure 130A has been dispensed by the dispensing element into a container 132 or a medication 110 has been dispensed by the dispensing element into a container 132 during time period 131A.

Thus, based on data 178, the computer is arranged to generate regimen 128 by modifying regimen 128A, for example, modifying measure 130A to generate measure 130 or modifying time period 131A to generate time period 131.

In an example embodiment, following the receipt of data 178 and the dispensing of medication 110 according to regimen 128 calculated using data 178, the computer is arranged to receive physiological data 180. Using data 180, the computer is arranged to modify regimen 128, for example, by modifying one or both of measure 130 or time period 131. The dispensing element is arranged to dispense an amount of medication 110 substantially equal to measure 130 or dispense medication 110 during time period 131. In an example embodiment, the dispensing element dispenses an amount of medication 110 substantially equal to measure 130 during time period 131.

In an example embodiment, the user interface is arranged to receive data 178 or 180 and to transmit data 178 and data 180 to the computer. For example, using a keyboard or voice recognition, the patient or other user can enter data 178 or 180. Data 178 or 180 can be any physiological data known in the art, including, but not limited to, blood sugar level, blood pressure, electrocardiogram data, pulse rate, respiration rate, blood gases, liver function enzymes, aspartate transaminase, thyroid function, heart function and risk indicators, hormone level, or antibiotic level.

In an example embodiment, the computer is arranged to receive data 178 or 180 from device 182 interfaced with the patient to generate data 178 or 180. For example, device 182 is any device known in the art for producing physiological data, including, but not limited to a blood pressure cuff, an electro-cardiograph device, a glucose meter, a blood gas meter, a respiration meter, or a pulse meter.

Dosage Not Taken at Expected Time: In an example embodiment, medication device 106 is arranged to dispense measure 130 of medication 110 only during time period 131. For example, if measure 130 is time sensitive, for example, dependent upon or fixed to period 131, medication device 106 does not, at least initially, dispense medication 110 when a request for medication 110, for example, signal 136, falls outside of time period 131. When medication 110 is not dispensed within time period 131, the computer is arranged to calculate, re-calculate, or modify regimen 128 according to when medication 110 is actually to be dispensed. For example, the computer is arranged to receive signal 136 at a time following the expiration of time period 131 and to calculate, re-calculate, or modify regimen 128 according to the time following the expiration of time period 131. Thus, the computer accounts for time sensitive changes to regimen 128. For example, the therapeutic affects of medication 110 may be time-sensitive and measure 130 may need to be increased due to the time difference between the expiration of time period 131 and the receipt of signal 136.

In an example embodiment, medication device 106 outputs information, for example, using user interface 138, regarding the discrepancy with respect to time period 131. In an example embodiment, medication device 106 transmits information regarding the discrepancy with respect to time period 131 to a remote system, for example, computer 172.

Regimen Calculated, Re-Calculated, or Modified According to Previous Dosage: In an example embodiment, the computer is arranged to calculate a point in time at which a previous dosage of medication 110 was dispensed by the medication device and to calculate, re-calculate, or modify regimen 128 according to when medication 110 was last dispensed. Thus, the computer can account for impacts on regimen 128 and the efficacy of medication 110 due to the time of the previous dosage of medication 110. For example, measure 130 may be progressively increased as the duration since the previous dosage of medication 110 increases.

Regimen Calculated, Re-Calculated, or Modified According to Time of Day: In an example embodiment, the computer is arranged to calculate, re-calculate, or modify regimen 128 according to the time of day when signal 136 is received or according to a predetermined time of day. For example, the therapeutic affect of medication 110 may vary according to the expected daily cycles of the patient, such as an expected decrease in physical activity late in the evening or at night and computer 102 calculates, re-calculates, or modifies regimen 128 according to such variances. In an example embodiment, the computer determines an optimum time of day for administering medication 110 and calculates measure 130 and time period 131 accordingly.

Monitor P.R.N. Compliance: In an example embodiment, regimen 128 includes time span 184 and threshold measure 186, and the computer is arranged to receive signal 136 requesting a dosage of medication 110, for example, according to measure 130, at a particular time. In an example embodiment, the computer is arranged to determine whether the request is in compliance with regimen 128 by: determining that a time period between a point in time for the previous dose of medication 110 and the particular time is no greater than time span 184; or, by determining that an amount of medication 110 dispensed by the dispensing element since an initiation of regimen 128 up to receipt of signal 136 is no greater than threshold measure 186. The computer is arranged to enable dispensing of medication 110 only if the request in signal 136 is in compliance with regimen 128.

Thus, the computer advantageously monitors compliance for p.r.n. (when necessary) medication regimens, that is, regimens in which the medication is dispensed in response to a request by the patient, rather than by a set schedule. To avoid excessive dosing by the patient, the computer keeps track of when a last dosage was administered and blocks administration of the next dosage if the time interval since the last dosage is not long enough (must be greater than time span 184). Apparatus 100 also block administration of medication 110 if the total amount of medication 110 dispensed since the on-set of a dosage period is too great (exceeds threshold measure 186). Apparatus 100 also can transmit information to various concerned parties, for example, via computer 172, regarding compliance with regimen 128.

Regimen Calculated, Re-Calculated, or Modified According to Medication Interaction: In an example embodiment, the patient is receiving one or more second medications in addition to medication 110. The computer is arranged to access history 188 of the administration of the addition medications, for example, an identification of the medications, dosages of the medications, and the times at which previous dosages were administered, and is arranged to calculate medication regimen 128 for the patient using the history. For example, measure 130 and/or time period 131 are calculated using history 188. Thus, the computer dynamically accounts for the impact of other medications on the administration of medication 110 and calculates or modifies regimen 128 accordingly.

Multiple Medications for a Single Patient: In an example embodiment, apparatus 100 is used to administer more than one medication for a patient. The computer is arranged to calculate, re-calculate, or modify regimen 128 for each orally-administered or injectable medication to be dispensed to the patient. In general, the discussion above regarding calculating, re-calculating, or modifying regimen 128 for a single medication 110, and the implementation of a single regimen 128 for a single medication 110, is applicable to regimen 128 including multiple medications. In an example embodiment, the interaction of the various medications to be administered to the patient is accounted for in the calculation of the regimen 128 for multiple medications 110. For example, time periods 131 can be calculated to properly space administration of the multiple medications to enhance the therapeutic affects of the medications or to avoid undesirable interaction of the medications.

Multiple Patients: It should be understood that the discussion above regarding apparatus 100 and a single patient is generally applicable to the discussion that follows regarding the use of apparatus 100 for a plurality of patients. In an example embodiment, the computer is used to calculate, re-calculate, or modify respective medical regimens for a plurality of patients and to execute the respective medical regimens. For example, apparatus 100 can be used in an institutional, clinical, or hospital setting to serve a larger population of patients. Thus, in a process similar to that described for a single patient, the computer is arranged to calculate, re-calculate, or modify a respective medication regimen 128 for each patient in a plurality of patients. The respective regimens include designations of respective measures 130 for respective orally-administered or injectable medications or respective designated time periods 131. In an example embodiment, respective regimens 128 include respective measures 130 and respective time periods 131. It should be understood that the respective orally-administered or injectable medications can be the same or different. For example, a same orally-administered or injectable medication can be dispensed to a plurality of patients, or respective different orally-administered or injectable medications can be administered to a plurality of patients. Also, respective measures 130 and time periods 131 can be the same or can vary according to the respective regimens. In an example embodiment, for a same medication 110, respective regimens 128 for a plurality of patients can vary according to factors, unique to respective patients in the plurality of patients, such as other medications being taken by the respective patients, or specific medical conditions of the respective patients.

In an example embodiment, the dispensing element is arranged to extract respective medications 110 from the medication storage element and non-intravenously dispense respective amounts of respective medications 110, substantially equal to respective measures 130, into respective containers 132. In an example embodiment, the dispensing element is arranged to extract respective medications 110 from the medication storage element and non-intravenously dispense respective medications 110 into respective containers 132 during respective time periods 131. In an example embodiment, the dispensing element is arranged to extract respective medications 110 from the medication storage element and non-intravenously dispense respective amounts of medication 110, substantially equal to respective measures 130, into respective containers 132 during respective time periods 131. Thus, the computer can accommodate a plurality of patients with respective pluralities of medical regimens including different medications and different dosages.

Computer 102 Remote From Device 106: As noted above, computer 102 can be located remote from medication device 106, for example, associated with website 131 or connected via a LAN. The discussion above regarding the operation of computer 102 is applicable to remote computer 102. Thus, the various operations, such as calculating, re-calculating, or modifying regimen 128, or transmitting information to computer 172 can be performed by remote computer 102. Advantageously, remotely locating computer 102 can enable greater security for sensitive information regarding patient identity, regimen 128, patient health care records, or payment arrangements.

Computer 102 On-Board The Cartridge: In an example embodiment, operations described for computer 102 are implemented by module 127. In this case, the discussion above regarding the operation of computer 102 is applicable to module 127. Thus, the various operations, such as calculating, re-calculating, or modifying regimen 128, or transmitting information to computer 172 can be performed by the module. Information applicable to the operation of module 127 is found in commonly owned U.S. Pat. No. 6,940,613, the disclosure of which is incorporated herein by reference in its entirety.

Integrated Computing Arrangement: In an example embodiment, the operations described above for computer 102 are implemented by a combination of integrated computing components located remote from medication device 106 (for example associated with website 131 or connected by a LAN), computing components part of medication device 106 and separate from the cartridge, and/or module 127. How the various operations are assigned can be determined by a variety of considerations such as security of patient information, ease of implementation, and fabrication and implementation costs. For example, sensitive patient information may be best protected in a more robust environment afforded by remote computing components. Therefore, operations requiring the use of such information can be implemented by the remote computing components. For example, regimen 128 can be calculated, re-calculated, or modified by the remote computing components and data necessary to implement the regimen, such as measure 130, can be transmitted to device 106 for implementation using computing components onboard device 106 or module 127.

Certain operations, such as the inventory control and replenishment operations, or the re-ordering operations described above may require, or may best be implemented by, computing components onboard device 106 or module 127.

Security Considerations: As noted above, protection of sensitive patient information can be enhanced by storing such information in a more robust remotely located computer system. For example, such protection may be necessary to comply with regulatory requirements, such as the Health Insurance Portability and Accountability Act of 1996 (HIPAA). In addition, further security can be enabled at medication device 106 by the input of biometric data to identify a patient to ensure that the patient requesting medication 110 and the patient for whom medication 110 has been prescribed are the same. Any biometric data known in the art can be used and any device known in the art for acquiring such biometric data can be used. In an example embodiment, cartridges 126 are secured to medication device 106, for example, the cartridges are locked to prevent unauthorized removal or replacement of the cartridges. Such an arrangement is particularly applicable to an institutional or clinical setting or for proscribed medications such as narcotics.

Dynamic Medication Regimen: Computer 102 enables dynamic calculation and modification of medication regimens in real time using real time data. Thus, the computer enables a medication regimen to be specifically adapted to the particular parameters of a particular patient at a particular time. As a result, optimum efficacy of an orally-administered or injectable medication is obtained. The computer also enables advantageous flexibility in the administration of orally-administered or injectable medications. For example, as noted above, an iterative process may be required before a proper dose of a medication is established. Also as noted above, such a process using known means is hampered by the limited doses available for most medications, in particular, medications in pill form. However, by using computer 102, virtually any dosage of a medication can be made available enabling a far more accurate and sensitive process, for example, a final dosage is not limited to one of a limited number of available dosages. Further, the waste associated with the use of medications in fixed dosages is eliminated (medications used in the iterative process and not containing the final dosage are discarded by current methods), since each dosage is individually metered.

The Medical Home: Apparatus 100 and computer 102 greatly facilitate the movement toward the "medical home," that is, moving as much patient care from an institutional setting to a home setting. Such movement decreases the cost of care and improves patient outcomes. A key stumbling block to the medical home is the administration of medications which have critical parameters, such as doses or schedules for doses. Due to the critical nature of such regimens, patients may be forced to stay in an institutional setting merely to ensure proper administration of the medications, although the patients may be otherwise fit to return to their homes. Also, patients may be forced to stay in an institutional setting to establish proper regimen parameters and to monitor and adjust such parameters, since the limited dosage levels currently available for medications complicate and extend this process.

However, using apparatus 100 and computer 102 in a patient's home, medications can be stored, metered, and dispensed in a highly accurate manner and compliance of the patient with the regimen can be closely monitored. For example, the computer can determine when dosages are actually taken and can monitor and control p.r.n. applications. Further, adjustments to a regimen can be made dynamically and in real time, minimizing the need for the type of oversight provided in an institutional setting. Also, apparatus 100 and computer 102 can communicate with outside agencies associated with the patient's health care, such as health care practitioners, medication prescribers, medication suppliers, and insurance companies. For example, information regarding compliance with a medication regimens and adjustments to medication regiments can be automatically compiled and transmitted to such agencies by computer 102. Thus, apparatus 100 and computer 102 can improve outcomes for patients while reducing costs and improving communication among outside agencies.

Institutional Settings: Apparatus 100 and computer 102 can provide a centralized means of accurately and securely storing, metering, and dispensing a plurality of medications for a plurality of patients in an institutional setting, such as a clinic, hospital, or residential facility.

Apparatus 100 can be mounted on a mobile platform enabling medical personal to wheel the apparatus to the location, for example, a room in a residential facility, where medication is to be dispensed. As noted above, apparatus 100 and computer 102 can provide a means of compiling and transmitting information for a large number of patients having different medication regimens.

Increased Accuracy: Advantageously, the computer enables a heretofore unobtainable degree of accuracy for the dispensing of an orally-administered or injectable medication. In an example embodiment, the dispensing element is arranged to meter and dispense medication 110 with an accuracy of approximately one part in a thousand. As noted above, dose variation in routine nursing is in the 1-10% range. Medication concentrations tend to be calibrated to support 1-10 cc measurements. Therefore, the accuracy of approximately one part in a thousand is a 10 to 100 fold increase over accuracy associated with current practice.

Further Considerations: Any means known in the art can be used to clean and sterilize device 106. For example cleaning fluid or alcohol can be passed through the dispensing device. The cleaning fluid or alcohol can be administered using a cartridge similar to cartridge 126. In an example embodiment, cooling or heating for medications is provided in device 106. For example, cartridges 126 can be provided with individual heating/cooling systems in the form of bi-metallic cooler/heaters. Also, a space enclosing cartridges 126 in device 106 can be heated or cooled.

It will be appreciated that various of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A computer-based apparatus for dispensing a medication, comprising:
   at least one specially programmed computer; and,
   a medication device, wherein:
      the at least one specially programmed computer is arranged to automatically generate a first medication regimen for a first patient, the first medication regimen including designation of a first measure for a first orally-administered or injectable medication; or automatically modify a first medication regimen for a first patient, by modifying a designation of a first measure for a first orally-administered or injectable medication; and,
      the medication device is arranged to:
         extract the first orally-administered or injectable medication from a medication storage element; and,
         non-intravenously dispense a first amount of the first orally-administered or injectable medication equal to the first designated measure or the modified first designated measure into a container.

2. The computer-based apparatus of claim 1, wherein the at least one specially programmed computer is arranged to:
   receive a real time input; and,
   automatically generate or modify the first medication regimen using the real time input.

3. The computer-based apparatus of claim 1, wherein:
   the medication storage element is insertable in and removable from the medication device to enable the medication storage element to be replaced when the first orally-administered or injectable medication in the medication storage element is depleted; and,
   the at least one specially programmed computer is: part of the medication device not including the medication storage element; attached to the medication storage element; or located remote from the medication device.

4. The computer-based apparatus of claim 1, wherein:
   the first medication regimen includes information as to whether a water-based liquid vehicle substance or a fat-based liquid vehicle substance is required for the first orally-administered or injectable medication; and,
   the medication device is arranged to dispense a water-based liquid vehicle substance or a fat-based liquid vehicle substance into the container.

5. The computer-based apparatus of claim 4, wherein:
   the at least one specially programmed computer is included in an electronic health record system or in an authorized order entry system; or,
   the at least one specially programmed computer is in communication with an electronic health record system or with an authorized order entry system.

6. The computer-based apparatus of claim 1, wherein:
   the medication device includes a chamber; and,
   the medication device is arranged to:
      receive a metering control signal;
      execute, in response to the metering control signal, a cycle by:
         transporting first orally-administered or injectable medication from the medication storage element into the chamber;
         displacing a known amount of the first orally-administered or injectable medication, transported into the chamber, through the nozzle; and,
      repeat the cycle such that a measure of the first orally-administered or injectable medication displaced through the nozzle is equal to the first amount.

7. The computer-based apparatus of claim 6, wherein:
   the medication device includes a displacement element arranged to transport the first orally-administered or injectable medication into the chamber using a vacuum, gravity, or capillary action; or,
   the displacement element includes a piezoelectric transducer.

8. The computer-based apparatus of claim 1, wherein:
   the medication device includes a chamber and a nozzle; and,
   in response to a metering control signal, the displacement element is arranged to:
      extract first orally-administered or injectable medication from the medication storage element;
      expel first orally-administered or injectable medication through the nozzle at a known flow rate; and,
      terminate operation of the displacement element when the amount of the first orally-administered or injectable medication expelled through the nozzle is substantially equal to the first measure.

9. The computer-based apparatus of claim 1 wherein the medication device is arranged to dispense the first orally-administered or injectable medication with a range of accuracy of approximately one part in a thousand.

10. The computer-based apparatus of claim 1, wherein:
the medication storage element includes a cartridge; and,
the at least one specially programmed computer is arranged to:
identify an orally-administered or injectable medication stored in the cartridge;
determine if the orally-administered or injectable medication stored in the cartridge is included in any medication regimen for the first patient; and,
transmit a warning signal if the orally-administered or injectable medication stored in the cartridge is not included in any medication regimen for the first patient.

11. The computer-based apparatus of claim 1, wherein the at least one specially programmed computer is arranged to:
identify a point in time at which the medication storage element is installed in the apparatus;
compare the point in time to a time period at which it was desired to install the medication storage element; and,
transmit a compliance signal to a computer associated with an entity selected from the group consisting of an insurance company, a health care provider, a health care facility, an entity supplying the medication storage element, and a health care records system, indicating whether the point in time fell within the time period.

12. An apparatus for storing and dispensing a medication, comprising:
a medication device; and,
a cartridge including:
a cavity for storing an orally-administered or injectable medication; and,
a module, including at least one computer, generating and storing information regarding the orally-administered or injectable medication, wherein:
the at least one specially programmed computer is arranged to automatically generate a first medication regimen for a first patient, the first medication regimen including designation of a first measure for a first orally-administered or injectable medication; or automatically modify a first medication regimen for a first patient, by modifying a designation of a first measure for a first orally-administered or injectable medication;
the medication device is arranged to:
extract the first orally-administered or injectable medication from the cartridge; and,
non-intravenously dispense a first amount of the first orally-administered or injectable medication equal to the first designated measure or the modified first designated measure into a container separated from the cartridge; and,
the cartridge is insertable in and removable from the medication device.

13. The apparatus of claim 12, wherein:
the information includes an amount of the orally-administered or injectable medication present in the cartridge; and,
the module is arranged to transmit a signal including the amount of the orally-administered or injectable medication present in the cartridge.

14. The apparatus of claim 12, wherein the module is arranged to:
receive a signal including modifications to the information; and,
modify the information according to the signal.

15. A computer-based apparatus for dispensing a medication, comprising:
at least one specially programmed computer; and,
a medication device, wherein:
the at least one specially programmed computer is arranged to automatically generate a medication regimen for a patient, the medication regimen including designation of a measure for an orally-administered or injectable medication; or automatically modify a medication regimen for a patient, by modifying a designation of a measure for an orally-administered or injectable medication; and,
the medication device is arranged to:
extract the orally-administered or injectable medication from a medication storage element;
mix a separate substance with the extracted orally-administered or injectable medication;
non-intravenously dispense an amount of the orally-administered or injectable medication, mixed with the separate substance, equal to the designated measure or the modified designated measure into a container separate from the medication device.

16. A medication device for dispensing a medication, comprising:
at least one computer;
a cartridge; and,
a dispensing element including:
a chamber; and,
a nozzle, wherein the dispensing element is arranged to:
receive a metering control signal from the at least one computer; and,
execute, in response to the metering control signal, a cycle by:
transporting orally-administered or injectable medication from the cartridge into the chamber;
displacing a known amount of the orally-administered or injectable medication, transported into the chamber, through the nozzle into a container separate from the cartridge; and,
repeat the cycle such that a measure of the orally-administered or injectable medication displaced through the nozzle is equal an amount included in a medication regimen for the orally-administered or injectable medication.

17. A computer-based apparatus for dispensing a medication, comprising:
at least one specially programmed computer; and,
a medication device including:
a cartridge; and,
a dispensing element, wherein:
the at least one specially programmed computer is arranged to automatically modify a medication regimen for a patient, by modifying a designation of a measure for an orally-administered or injectable medication;
the dispensing element is arranged to:
extract the orally-administered or injectable medication from the cartridge; and,
non-intravenously dispense an amount of the orally-administered or injectable medication equal to the modified designated measure into a container separate from the cartridge;
the at least one specially programmed computer is arranged to:

identify an orally-administered or injectable medication stored in the cartridge;

determine if the orally-administered or injectable medication stored in the cartridge is included in any medication regimen for the patient; and, transmit a warning signal if the orally-administered or injectable medication stored in the cartridge is not included in any medication regimen for the patient.

* * * * *